United States Patent
Leeb et al.

[11] Patent Number: 5,830,207
[45] Date of Patent: *Nov. 3, 1998

[54] ELECTROMAGNETICALLY TRIGGERED, RESPONSIVE GEL BASED DRUG DELIVERY DEVICE

[75] Inventors: Steven B. Leeb, Belmont; Elmer C. Lupton, Boston; Xiaohong Yu, Boston; George Hovorka, Boston, all of Mass.

[73] Assignee: MedLogic Global Corporation, Colorado Springs, Colo.

[*] Notice: The term of this patent shall not extend beyond the expiration date of Pat. No. 5,643,246.

[21] Appl. No.: 791,368

[22] Filed: Jan. 30, 1997

Related U.S. Application Data

[63] Continuation of Ser. No. 393,971, Feb. 24, 1995, Pat. No. 5,643,246.

[51] Int. Cl.$^6$ ........................ A61K 9/22
[52] U.S. Cl. ................... 604/890.1; 128/899
[58] Field of Search ................. 604/890.1, 891.1, 604/49, 131, 246; 128/899; 600/9–14

[56] References Cited

U.S. PATENT DOCUMENTS

| | | |
|---|---|---|
| 4,545,368 | 10/1985 | Rand et al. . |
| 4,657,543 | 4/1987 | Langer et al. . |
| 4,662,359 | 5/1987 | Gordon . |
| 4,735,796 | 4/1988 | Gordon . |
| 4,767,611 | 8/1988 | Gordon . |
| 4,827,945 | 5/1989 | Groman et al. . |
| 5,019,372 | 5/1991 | Folkman et al. . |
| 5,152,758 | 10/1992 | Kaetsu et al. . |
| 5,226,902 | 7/1993 | Bae et al. . |
| 5,366,454 | 11/1994 | Currie et al. . |

OTHER PUBLICATIONS

Wust et al., "Strategies for Optimized Application of Annular–Phased–Array Systems in Clinical Hyperthermia" *Int. J. Hyperthermia*, 7(1), 157–173 (1991).

Lee et al., "Potential Hazards of Radiative Electromagnetic Hyperthermia in the Presence of Multiple Metallic Surgical Clips" *Int. J. Hyperthermia*, 8(6), 809–817 (1992).

Thrall et al., "Serious Toxicity Associated with Annular Microwave Array Induction of Whole–Body Hyperthermia in Normal Dogs" *Int. J. Hyperthermia*, 8(1), 23–32 (1992).

Brezovich et al., "Hyperthermia of Pet Animal Tumours with Self–Regulating Ferromagnetic Thermoseeds" *Int. J. Hyperthermia*, 6(1), 117–130 (1990).

Oleson, "Hyperthermia by Magnetic Induction: I. Physical Characteristics of the Technique" *Int. J. Radiation Oncology Biol. Phys.*, 8, 1747–1756 (1982).

Halac et al., "Magnetic Induction Heating of Tissue: Numerical Evaluation of Tumor Temperature Distributions" *Int. J. Radiation Oncology Biol. Phys.*, 9, 881–891 (1983).

Jordan et al., "Inductive Heating of Ferrimagnetic Particles and Magentic Fluids: Physical Evaluation of their Potential for Hyperthermia" *Int. J. Hyperthermia*, 9(1), 51–68 (1993).

*Primary Examiner*—John P. Lacyk
*Assistant Examiner*—Samuel Gilbert
*Attorney, Agent, or Firm*—Burns, Doane, Swecker & Mathis, L.L.P.

[57] ABSTRACT

A system for remotely inducing a phase transition in a gel is provided. The system includes a gel capable of volume change in response to an environmental stimulus, a seed material in contact with the gel, and generating a time-varying magnetic or a time-varying electric or electromagnetic field in the proximity of the gel to produce the environmental stimulus. In a preferred embodiment, the environmental stimulus is temperature.

16 Claims, 2 Drawing Sheets

ELECTROMAGNETICALLY TRIGGERED, RESPONSIVE GEL BASED DRUG DELIVERY DEVICE

CROSS REFERENCE TO RELATED APPLICATION

This application is a continuation application of U.S. Ser. No. 08/393,971, filed Feb. 24, 1995, now U.S. Pat. No. 5,643,246 issued Jul. 1, 1997 and which is incorporated herein by reference.

FIELD OF THE INVENTION

The present invention relates to polymer gels capable of undergoing reversible and dramatic volume changes in response to an environmental stimulus. The present invention further relates to the application of an environmental stimulus remote from the gel. The present invention further relates to a device and process for triggered delivery of biologically active materials.

BACKGROUND OF THE INVENTION

A gel consists of a cross-linked network of polymers swollen in a solvent. Under certain conditions, gels have been observed to undergo abrupt, reversible changes in volume. The volume change may be continuous or discontinuous. As an external environmental condition (e.g., temperature, solvent composition, pH, electric field, light intensity, pressure, ionic strength, etc.) is changed, the polymer network contracts and/or expands in volume (i.e., the gel is a "responsive" gel). The volume of such a gel may, under certain circumstances, change reversibly by a factor as large as several hundred when the gel is presented with a change in external conditions. See, Tanaka Phys. Rev. Lett. 40(12), 820–823 (1978); Tanaka et al, Phys. Rev. Lett. 38(14), 771–774 (1977); Phys. Rev. Lett. 45(5), 1636 (1980); llavsky, Macromolecules 15, 782 (1982); Hrouz et al., Europ. Polym. J. 17, 361 (1981); Ohime et al, J. Chem. Phys. 8, 6379 (1984); Tanaka et al, Science 218, 462 (1982); llavsky et al, Polym. Bull. 7, 107 (1982); Gehrke, Responsive Gels: Volume Transitions II; Editor: K. Dusek Springer-Verlag New York, N.Y., pp. 81–144 (1993); Li et al, Annual Rev. Mater. Sci. 22, 243–77 (1992); and Galaev et al, Enzyme Microb. Technol. 15, 354–66 (1993), all of which are incorporated by reference. Because the volume change occurs in response to an external environmental stimulus, these gels are known as "responsive gels".

Responsive gels may be used as actuators suitable for application in servomechanisms and sensors, ranging from microscopic (silicon) mechanisms to larger devices comparable in size and force density to biological systems. For example, responsive gel actuators may be used as synthetic muscles which provide direct linear motion quietly, swiftly, and with useful force densities. Gels loaded with appropriate, beneficial solvents could be used in drug-release applications either in vivo or in vitro, releasing the solvent under appropriate environmental conditions. They could also be used to release or separate substances in a wide range of organic and inorganic chemical processes. Responsive gels have been used to encapsulate and release a variety of biologically active chemicals including pharmaceuticals such as ibuprofin and enzymes. The tremendous range of potential applications for gels is due in part to the large number of potential environmental conditions that can be used to induce a volume change in the gel.

In many of these applications, it is difficult to directly introduce the environmental change necessary to induce (or "trigger") the desired volume change in the gel. For example, it may be difficult to directly heat in the vicinity of a synthetic muscle deeply imbedded in a servomechanism or a drug delivery device located in vivo. A method for remotely activating a gel phase transition is desirable under these circumstances. Preferably, such a remote triggering method is non-intrusive. In addition, the method of remotely activating a gel phase transition should provide for the local, and not systemic, administration of the environmental "trigger".

Although electromagnetic radiation has been used in connection with animal or human tissue, it has the disadvantage that it can interact strongly with the tissue to produce undesirable effects. Examples range from sunburn caused by ultraviolet light or bulk heating and cooking caused by microwave radiation.

Animal tissue is relatively transparent to a static or quasi-static electric or magnetic field. Remote heating of animal or human tissue has been accomplished by the implantation of particulate magnetic material into the animal tissue, followed by application of a magnetic field to the area. In this case, the magnetic material may couple with the magnetic field to generate heat through hysteresis and eddy current. However, there has been no application of magnetically induced remote heating to gels or to hydrous materials other than animal tissue.

It is the object of the present invention to provide a system and method for remotely triggering gels to undergo a phase transition. It is a further object of the present invention to induce a phase transition in a gel by application of a magnetic, electric or electromagnetic field. It is yet a further object of the present invention to provide a system for remotely triggered delivery of drugs.

SUMMARY OF THE INVENTION

The present invention pertains, in part, to electromagnetically triggered, responsive gel based drug delivery devices. The devices include polymer gels capable of undergoing reversible volumetric changes in response to an environmental stimulus which is remote from the gel.

By quasi-static field, as that term is used herein, it is meant that the field frequency is small compared to the speed of light divided by the largest length D, where D is a dimension of the system such as the length of a gel. This is equivalent to saying that the primary energy storage and transfer occurs through either the electric or magnetic field. In preferred embodiments, quasi-static fields would be in the frequency range of about 0 to approximately 10 MHz to satisfy the quasi-static approximation in typical human body dimensions. An electromagnetic wave or radiation exhibits comparable energy levels in coupled electric and magnetic fields.

A "gel", as used herein, is a material between the solid and liquid state, in which a pure or mixed solvent or solution is entrained within a crosslinked polymer network. By "pure or mixed solvent and/or solution", as stated herein, it is recognized that a mixture of solvents may be absorbed by the polymer network. Additionally, the solvent may include salts or other additives so as to form a solution, which may also be absorbed or entrained within the polymer network. The solvent may be water or an organic compound.

A "responsive gel", as used herein, is a gel which will undergo reversible swelling (entraining solvent) and collapsing (releasing solvent) upon exposure to an external environmental condition, such as, for example, temperature, pH, solvent concentration, electric field, photon irradiation, solution ionic strength and pressure. In particular, the responsive gel is responsive to temperature. In order to be classified as a "responsive" gel, the gel must respond to a very small change in environmental conditions A volumetric change of at least 20 percent in response to the small change in environmental stimulus is typical, in which the gel expands from a less liquid-filled state (collapsed state) or a dry state to a more liquid-filled stated (expanded state), or vice versa. When that solvent is water, or substantially water, the gel is known as a "responsive hydrogel".

By a "biologically active material", it is meant a chemical which will interact with biological systems to change or potentially change in a measurable way, the functioning of the system. Examples of biologically active materials are drugs, pharmaceuticals and enzymes.

A "seed material" may be a magnetic receptor, an electric receptor or an electromagnetic receptor. A "magnetic receptor" is a material which will interact with a quasi-static time-varying magnetic field to dissipate energy. An "electric receptor" is a material which will interact with a quasi-static time-varying electric field to dissipate energy. An "electromagnetic receptor" is a material which will interact with an electromagnetic field to dissipate energy.

By "remotely" triggered, as that term is used herein, it is meant that the phase transition is induced without physical contact of the primary stimulus, i.e., the electromagnetic field, with the gel.

In one embodiment of the invention, a system which is capable of remotely inducing a phase transition in a gel is provided. The system includes a gel capable of a volume change in response to an environmental stimulus, a magnetic receptor which is in contact with the gel, and the generation of a time-varying magnetic field in the proximity of the gel to produce the environmental stimulus.

The time-varying magnetic field may be a quasi-static magnetic field. The magnetic receptor may be any material or material geometry with appropriate magnetic properties. For example, the magnetic receptor may be in the form of a film, a rod, a particle, a fluid, a glass-encased particle or a bead. Ferromagnetic materials, ferrites and iron-containing derivatives are illustrative of materials suitable for use as magnetic receptors in accordance with the invention.

In an alternative embodiment of the invention, another system which is capable of remotely inducing a phase transition in a gel is provided. In this embodiment, the system includes a gel capable of a volume change in response to an environmental stimulus as in the preceding embodiment, and an electric receptor which is in contact with the gel. The system also provides for the generation of a time-varying electric field in the proximity of the gel to produce the environmental stimulus.

In this embodiment, the time-varying electric field may be a quasistatic electric field. The electric receptor may be in the form of a film, a rod, a particle, a fluid, a glass-encased particle or a bead. Exemplary electric receptors include waxes, mica and polyester. In general, materials having a high dielectric constant are suitable for use as electric receptors in the present invention.

A further embodiment of the invention includes another system which is capable of remotely inducing a phase transition in a gel. In this embodiment, a gel which is capable of a volume change in response to an environmental stimulus is provided in contact with a seed material. The system provides for the generation of an electromagnetic field in proximity to the gel, thereby producing the environmental response.

The environmental stimulus may be a variety of stimuli. In a preferred embodiment, the environmental stimulus includes a change in temperature.

The gel may be selected from any gel which undergoes a phase transition upon exposure to an environmental stimulus. In a preferred embodiment, the gel is in the form of a bead. The material contained in the gel may also be selected from a variety of compounds, for example, an organic solvent. In a preferred embodiment, the gel contains a biologically active compound such that when the gel is exposed to an environmental stimulus, the biologically active compound is thereby released.

The present invention also provides a method for remotely inducing a phase transition in a gel. The method includes providing a gel in contact with a magnetic receptor. The gel is capable of a volume change in response to an environmental stimulus. A time-varying magnetic field is applied in the proximity of the gel such that the magnetic field generates a response in the magnetic receptor, thereby providing the environmental stimulus which induces the gel to undergo a change in volume.

BRIEF DESCRIPTION OF THE DRAWINGS

The invention will be understood with reference to the drawings, in which.

DETAILED DESCRIPTION OF THE INVENTION

Figure 1:
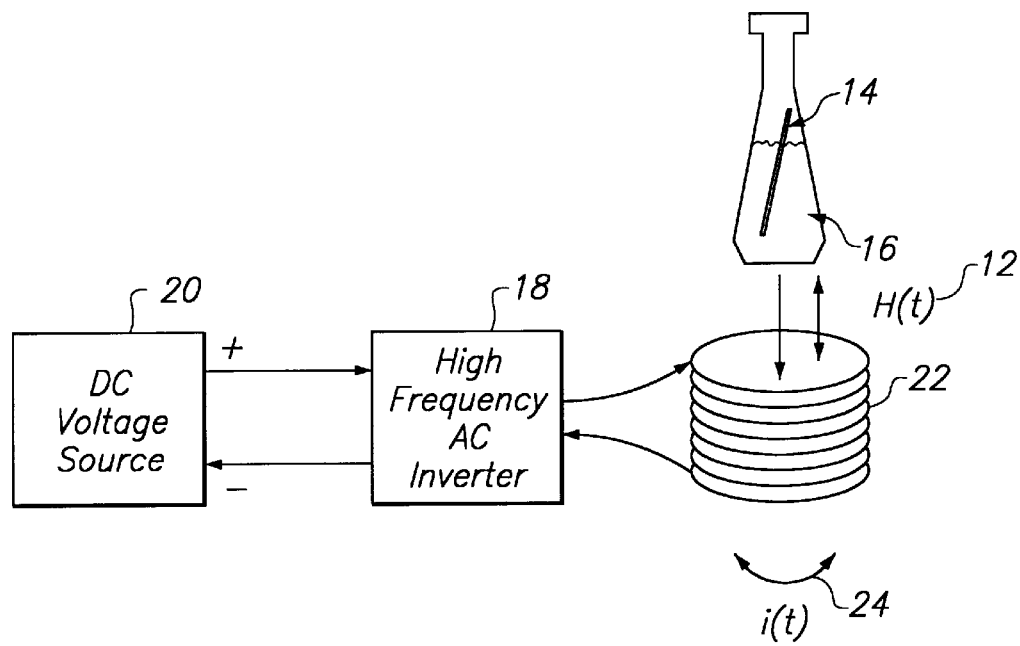
FIG. 1 is a schematic illustration of the system of the invention.

It is possible to induce a volume change (e.g., "trigger") in a gel with a time-varying, quasi-static magnetic field (e.g., through eddy current or hysteresis losses) or a time-varying quasi-static electric field (e.g., through dielectric losses) or with a radiating electromagnetic wave. The energy delivered by the applied fields could be used to trigger a gel, for example, by creating thermal losses through a combination of loss mechanisms. In each instance, a material sensitive to the applied field, referred to generally as the "seed material", is introduced into the gel. Heat generated by coupling of the seed material with the applied field triggers the gel phase transition.

While application of an electromagnetic field may be used to invoke any response in the seed material (e.g., a change in temperature, pH or chemical composition), the discussion which follows is directed mainly to heating. This is in no way to be considered limiting of the invention.

There are at least four loss mechanisms that could be chosen, by selecting an appropriate seed material and applied field, to create heating induced by a field. These mechanisms are eddy current heating, hysteresis heating or losses, dielectric heating and mechanical losses. Depending upon the nature of the applied field, different seed materials will be appropriate.

Eddy Currents: A time-varying magnetic field can cause current to flow in a material like copper or steel with reasonably high conductivity $\sigma$. This is predicted by Faraday's law, one of Maxwell's equations. In a material with finite conductivity, i.e., a material with some resistance, these currents can result in substantial thermal power dissipation. In the presence of high frequency magnetic fields, induced eddy currents may not flow through the bulk of the conductive material, instead flowing only in a thin surface region of the material due to a phenomenon called skin effect. The skin depth δ for a material is defined by the formula $$\delta = \sqrt{2/(\omega\mu\sigma)}$$

and serves as an indicator of the skin thickness in which current will flow. The variable ω represents the angular excitation frequency of the magnetic field, and μ represents the magnetic permeability of the material. For a given current, a small skin depth will result in higher power dissipation levels in a material, because the current is constrained to flow in a thinner material region with higher effective resistance. Notice that, for a given material conductivity, the skin depth can be reduced (increasing dissipation levels) by raising the magnetic field frequency or by employing a seed material with a higher magnetic permeability.

Hysteresis Losses: Ferromagnetic (magnetizable) materials, e.g., the metal in a typical paper clip that can be picked up with a permanent magnet, typically consist of microscopic magnetic domains. Loosely, these domains are crystalline regions of ordered structure in the material. All of the atoms in a domain share a common magnetic alignment. In short, a domain is a microscopic bit of material with a magnetic orientation like a permanent magnet. In a macroscopic, non-magnetized block of iron or other ferromagnetic receptor, the domains are randomly organized with respect to one another. Because of this random organization, the block exhibits no net magnetic orientation. The domains can be oriented to exhibit a net macroscopic magnetic field by aligning the domains with an applied magnetic field. For example, stroking a paper clip with a magnet will typically leave the clip with a lasting magnetization. This magnetized paper clip can be used to pick up other paper clips or bits of ferromagnetic receptor.

In the presence of a time-varying magnetic field, the domain orientation in a ferromagnetic block will vary along with the varying orientation of the applied field. Work is done by the magnetic field to orient the domains, and this work is dissipated as heat or domain "friction" as the domains "rub" against each other while aligning. The energy dissipated over a full cycle of magnetic excitation is proportional to the area of the B-H curve for the block material. Raising the frequency of the applied magnetic field increases the power dissipation as the B-H loop is traversed more frequently. Hence, this domain friction or hysteresis loss mechanism may be increased by raising the field excitation frequency, or by employing a material with a B-H loop with a greater area.

Dielectric Heating: Other materials may exhibit an electrostatic polarization at molecular levels. Much like the alignment of domains described above for hysteresis losses, these polarized charges in dielectric materials may be aligned by applying an electric field. A time-varying electric field induces a time-varying alignment of the charges. Work that is dissipated as heat is performed in the alignment process. Dielectric losses may be raised by increasing excitation frequency or by employing materials which are relatively more "lossy" dielectrics.

Mechanical Losses: Mechanical dissipation may be induced in a quasi-static field due to macroscopic motion within the gel. A low frequency (e.g., 60 Hz) electric or magnetic field produces motion of the seed material. As the seed material moves against the gel, friction and heat result.

All four of these loss mechanisms could be excited to some extent is by electromagnetic radiation, in which electric and magnetic fields coexist with comparable energy densities. Eddy currents and hysteresis losses could also be induced by a time-varying, quasi-static magnetic field. Dielectric heating may be induced by a time-varying quasi-static electric field. Dielectric losses are the primary heating mechanism in a quasi-static electric field. Mechanical losses may be induced by low frequencies, e.g., 60 Hz, in quasi-static fields. The term quasi-static implies that the excitation field frequency is small compared to the speed of light divided by the largest length, D, in the system. In such systems, approximately 90% of the energy may be in the stated electric or magnetic form. In electromagnetic radiation, the electric and magnetic field strengths are comparable. The term "quasi-static" applies under these circumstances because the magnetic or electric field remains unchanged (or essentially "static") across the entire gel system during the time it takes for light to propagate across the gel system.

Depending upon the particular application, selection of one or more fields may be appropriate. For example, electric fields do not penetrate deeply into animal tissue and are therefore inappropriate for triggering a gel deeply implanted within the organism, but may be well suited for surface treatments. Animal tissue is relatively transparent to a magnetic field, however, and is well suited for triggering phase changes in implanted gels.

The system of the present invention is described with reference to FIG. 1 which illustrates an alternating magnetic field is H(t) 12 used to heat a ferromagnetic steel pin (the "seed") 14 in contact with or embedded in a gel 16. The magnetic field induces eddy currents and hysteresis losses in the pin, causing the pin to heat up. The heat from the pin raises the temperature of the surrounding gel, causing a volume phase transition in the gel. Because the energy transfer to the pin/gel system occurs through a magnetic field, the system is contactless and may be used to trigger a gel subdermally, in vivo or in any remote location where an electromagnetic field could penetrate.

An alternating current (AC) inverter 18 may be used to generate a high frequency voltage waveform from a DC (direct current) source 20. This DC source may be generated by rectifying and filtering the electric utility voltage, or it could be provided by a battery or other DC source for portability. The high frequency voltage waveform is impressed across the terminals of a magnetic circuit which is depicted as a long, air-core solenoid 22 or cylindrical coil of wire in FIG. 1. The applied AC voltage causes a high frequency alternating current i(t) 24 to flow in the winding. The current flowing in the winding produces a high frequency, alternating magnetic field 12 in the coil 22. For a long solenoid, the magnetic field H(t) 12 as a function of time t inside the coil is approximately $$H(t) = \frac{Ni(t)}{d}$$

where N is the number of turns of wire in the coil, i(t) is the coil current as a function of time, and d is the height of the coil. The field outside the solenoid is approximately negligible. Note that other magnetic coil arrangements, e.g., a Helmholtz coil pair, could be employed instead of the solenoid. With a Helmholtz pair, a magnetic field could be induced in a region without having to surround the region with wire coils. Also, high frequency, high permeability materials like ferrite could be used with a winding or winding set to guide magnetic flux to a target location.

The magnetic field H(t) is used to induce the volume phase transition in the gel system of interest. In FIG. 1, the gel system is indicated schematically by the thin flask above the coil. The flask contains a quantity of gel beads 16 and a ferromagnetic metal pin 14 with reasonably high conductivity. When this bead-filled flask is inserted into the solenoid 22 (or the active region of whatever coil system is selected), the magnetic field H(t) 12 induces eddy-currents that flow in the steel and create ohmic losses, as described above. The magnetic field also induces hysteresis losses in the metal pin. If the magnetic field has sufficient amplitude and frequency, these two loss mechanisms will generate sufficient heat in the pin to warm the gel beads, inducing a reversible volume phase transition. When the magnetic field is removed, the eddy current and hysteresis losses will cease, the gel system will cool, and the gels will return to their initial state. Additional cooling mechanisms may be made available, where necessary and feasible, such as by way of example only, water cooled tubing.

The technology used to generate the quasi-static time-varying magnetic field may be designed to be aesthetically acceptable to the user. As an example, a solenoid may be designed to resemble a wristwatch or a cuff. A Helmholtz coil system may be designed to resemble two plates.

The magnetic field may be connected to a manual or automatic control device so that the field would be turned on to trigger the gel at a user-desired time. As an example, the gel could be loaded with a pain-killing drug and the user could trigger the release of the drug when desired. Alternatively, the gel could be loaded with a contraceptive drug and an automatic system would trigger the gel on a daily basis.

Suitable magnetic receptors.

Any material or material geometry with appropriate magnetic properties may be used as the magnetic receptor. For example, the magnetic receptor may be in the form of a pin or rod, or it may take the form of a container housing the gel which may heat the gel from the outside, or it may take the form of flakes, particles or beads dispersed in the gel. Materials suitable for remote heating by magnetic field include ferromagnetic materials and ferrites. In ferrites, adjacent magnetic moments are of opposite direction and unequal magnitude. In ferromagnetic materials, adjacent magnetic moments are parallel and equal in magnitude. The magnetic receptor may be a magnetic fluid, which is a suspension of ferromagnetic or ferrite particles of a size much smaller than the magnetic domain (1–100 nm), such that each particle possesses a magnetic dipole.

In instances where eddy current losses is the primary heating mechanism, it is desirable to have a material of high conductivity, such as by way of example only, copper and iron. In instances where hysteresis losses are the primary heating mechanism, it is desirable to have a material of high magnetic permeability, such as by way of example only, iron oxides and transition metals. In order to take advantage of both loss mechanisms, the material can possess both high conductivity and magnetic permeability. Iron is a good example of such a material. Also, ceramic glasses containing iron oxides or other transition metal ferrites may be preferred for uses where it is desirable to isolate the magnetic receptor from the host, particularly in instances where the magnetic receptor is toxic to the host, i.e., $Fe(OH)_3$. Ceramic materials of this nature are described in U.S. Pat. No. 4,323,056 to Borrelli et al, incorporated herein by reference.

The effectiveness and efficiency of the magnetic receptor is dependent upon its ability to translate magnetic energy into thermal energy. This ability is related to the crystal type and concentration and the presence of precrystalline or semiamorphous regions. Additionally, the coercive force exhibited by the magnetic receptor varies with the size of the crystalline domains and particle size and crystal grains size will be a factor.

We have observed that the orientation of an asymmetric magnetic receptor in a magnetic field can greatly influence the energy dissipated in the receptor. In particular, if a receptor which has a long dimension is oriented along the magnetic field lines, the degree of dissipation is observed to be much greater than if the long dimension is across the field lines. A "long dimension" means a maximum dimension which is at least twice the shortest dimension.

An effective amount of a magnetic receptor is in the range of about 1–80 percent by weight of the total gel system. By gel system, it is meant a gel, including absorbed solvent(s), and the magnetic receptor. In a preferred embodiment, the magnetic receptor comprises about 20–50 percent by weight of the gel system.

Suitable electric receptors. While not meant to be limiting, exemplary electric receptors include waxes, mica and polyester. In general, materials having a high dielectric constant are suitable for use as electric receptors in the present invention.

Suitable electromagnetic receptors. While not meant to be limiting, exemplary electromagnetic receptors include any conductive metal. Water, preferably at about 2 GHz, may also be used as an electromagnetic receptor.

Suitable gels.

The gel may be selected from any gel which undergoes a phase transition upon exposure to an environmental stimulus. This is most typically, but not exclusively, a change in temperature. Where it is contemplated that the gel is to be implanted in vivo, the gel must additionally be non-toxic to the host. Suitable gel compositions for that purpose include, but are in no way limited to, those described in copending U.S. Ser. No. 08/276,193 entitled "Novel Polymer Gel Networks and Methods of Uses" filed Jul. 18, 1994, incorporated herein by reference.

Other suitable gels include, by way of example only, hydroxypropyl cellulose (HPC) and methyl cellulose (MC), and mixtures thereof, optionally blended with hydroxyethyl cellulose (HEC), carboxymethyl cellulose (CMC), hydroxypropylmethyl cellulose (HPMC), ethylhydroxyethyl cellulose (EHEC), hydroxymethyl cellulose (HMC), and methylhydroxyethyl cellulose (MHEC) and mixtures thereof, the manufacture and use of which are described in co-pending U.S. Ser. No. 08/276,532, filed Jul. 18, 1994 and entitled "Useful Responsive Polymer Gel Beads", herein incorporated by reference.

Yet other suitable gels may also include gels which swell in organic media, such as benzene, acetone and the like. The manufacture of such gels is described in U.S. Ser. No. 08/114,494 filed Aug. 31, 1993 and entitled "Gels Which Exhibit Phase Transitions in an Organic Medium", incorporated herein by reference. These gels are given by way of example only and are not meant to be limiting of the invention. Any gel which exhibits a phase transition is considered within the scope of the invention.

The gel itself could be in any form that permits thermal contact between the seed and the gel. In a preferred embodiment, the gel is in the form of a bead. The manufacture of a gel bead is described in U.S. Ser. No. 08/276,532. Instead of beads, the gel may be, for instance, in the form of a solid cylinder, a sheet, or to conform with the shape of the flask or any other container.

EXAMPLE 1

Figure 2:
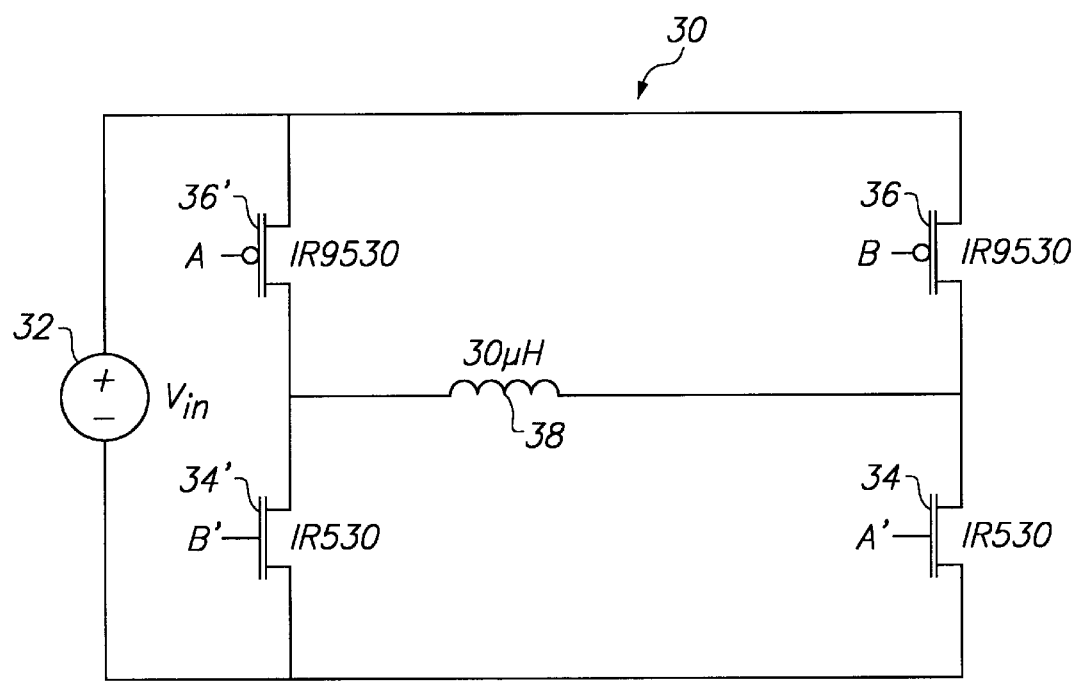
FIG. 2 is an electronic schematic diagram of a high frequency inverter which may be used in the system of the present invention.

A high frequency inverter and magnetic coil system 30 (see FIG. 2) have been constructed to test the design described in the previous section. The high frequency inverter can either operate from a DC power supply 32 powered by the electric utility or from a battery, for portability. A 15 volt battery pack provided the input to the inverter in the tests described below. The inverter is a full bridge that consists of four semiconductor power MOSFET switches. A schematic of the full bridge is shown in FIG. 2. The full bridge consists of two IRF530 N-channel MOSFETs 34, 34' and two IRF9530 P-channel MOSFETs 36, 36' operated as switches. The body diodes of the MOSFETs serve here as freewheeling diodes. Note that this is simply one arrangement for developing a high frequency AC waveform. There are a tremendous number of inverter circuit topologies and switching schemes that could be used for this application. With appropriate switching, an AC voltage waveform is developed across the center of the bridge, where a 30 $\mu$H air core solenoid 38 (indicated as an inductor in FIG. 2) is installed.

Figure 3:
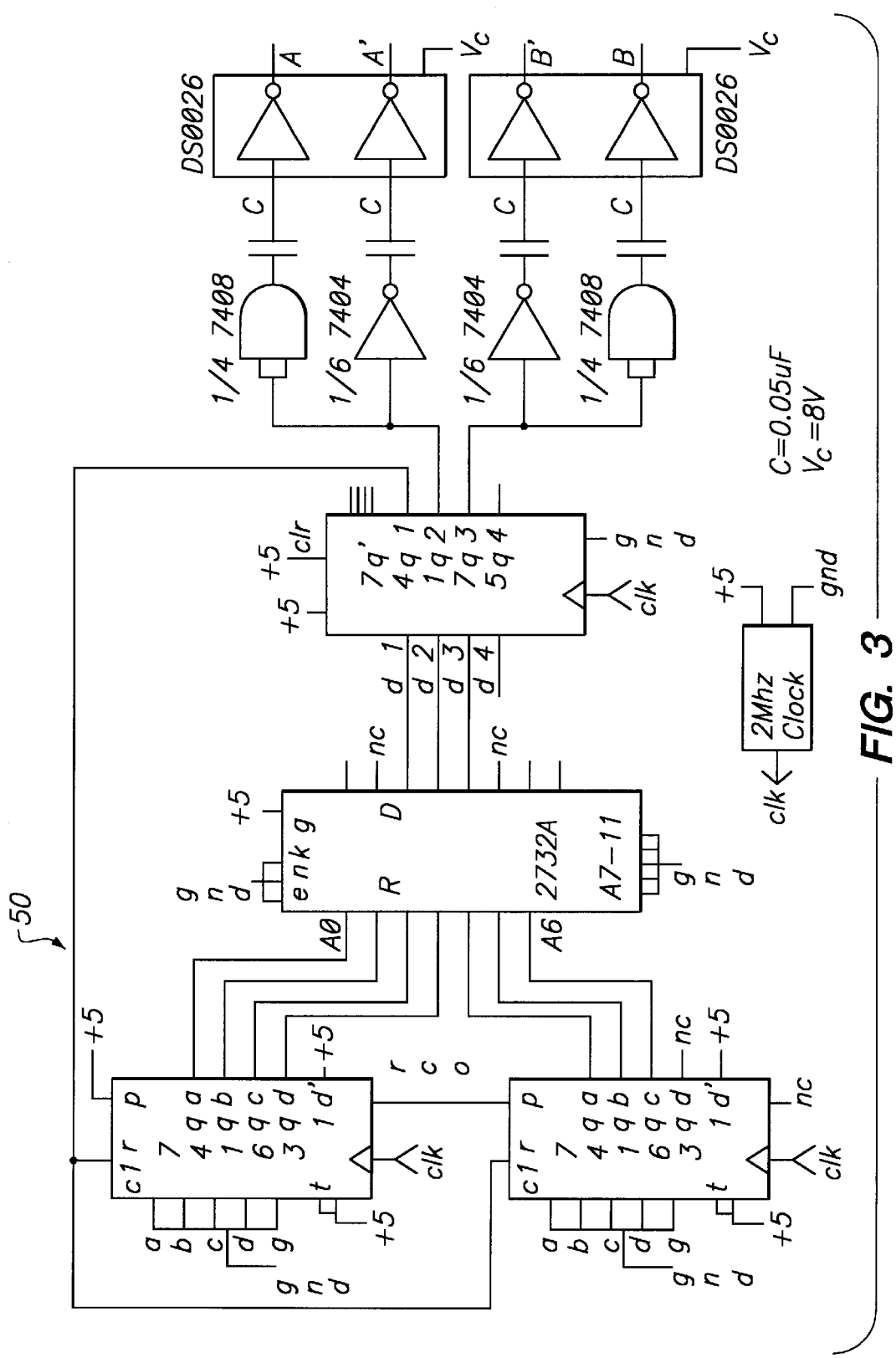
FIG. 3 is an electronic schematic diagram of a finite state machine controller which may be used in the system of the present invention.

The inverter is designed to deliver a fixed frequency (200 kHz) AC signal. A finite state machine (FSM) 50 configured as a programmable waveform synthesizer is used as the controller for the inverter. The FSM is shown in FIG. 3.

The 74163 counters in the FSM are clocked at 2 Mhz. They will count through a fixed number of addresses in a single AC period. At the end of this time, a control bit from the EPROM (q1 on the 74175) will clear the counters and the count will start over again. The first bit, q2 on the 743175 latch, is logic high most of the first half of the AC period, and zero the rest of the time. The second bit (q3 on the 74175) is high during the latter half of the AC period, and zero the rest of the time. When q2 is high, the channel A FETS (A drives the P-MOSFET, A' drives the N-MOSFET) are on. When q3 is high the channel B FETS are on (B drives the P-MOSFET, B' drives the N-MOSFET).

To prevent shoot-through, all channels are off for a short interval during the switch over from the A FETs on to the B FETS on. The presence of these "all off" bits guarantees a minimum time between the digital turn off command for one channel and the turn on command for the other. Note that other switching schemes could be used to improve the efficiency of the inverter. For example, by modifying the FSM to provide four separate drive signals, one for each MOSFET in the bridge, it would be possible to operate the bridge with resonant switch transitions that recover the energy stored in the solenoid and provide zero-voltage, lossless switching.

The inverter 30 described above was used to drive a 1 centimeter diameter, 30 $\mu$H solenoid, which applied a magnetic field at 200 kHz frequency. The solenoid was able to induce a reversible phase transition in a gel system like that described in the previous section, ie., gel beads and a steel pin in a glass tube, in approximately 2 minutes. A higher field strength in the solenoid, created, for example, by increasing the DC bus voltage, would heat the seed more swiftly. This, in turn, would induce the phase transition more swiftly. It was also noted that orientation of the seed pin affected the efficiency of heating. Orientation of the seed material perpendicular or parallel to the magnetic field may be a factor in optimization of the system.

EXAMPLE 2

This example illustrates a volumetric gel change using a magnetic receptor. A 10 mg gel swollen with water colored with blue dye and containing a magnetic receptor (½" long steel needle) was introduced into tissue. The tissue was then placed into a solenoid coil as described in Example 1. A magnetic field at 200 kHz frequency was applied. Within about 15 seconds, a phase transition occurred and about 9 mg, i:e. about 95%, of the solvent was released.

EXAMPLE 3

A gel was prepared as in Example 2 and placed in a Helmholtz coil pair. A magnetic field at 200 kHz frequency was applied and within about 45 seconds, a phase transition occurred and about 95% of the solvent was released from the gel.

EXAMPLE 4

This experiment illustrates mechanical losses in a low frequency field. Steel particles were prepared by grinding hot rolled steel with a W. F. Wells and Sons Model A6 horizontal band saw. These particles were then mixed in Master Mechanic Household Oil (Distributed by Cotter & Company, Chicago, ILL. 60614). Sufficient oil was added to form a slurry of particles in oil.

A solenoid coil was then wound on a ¾", schedule 40 plastic pipe coupling manufactured by Nibco. The internal diameter of the form was 1.05 inches and 2.05 inches long. Approximately 100 turns of No. 22 stranded wire was wound on this form and the coil was connected to a 24 volt filament transformer. This transformer was then attached through a variable auto-transformer to the supply mains.

The voltage across the coil was advanced until a magnetic field level of 22.1 gauss was obtained. This was measured with an E. M. F. 140-3-60 Gauss meter coil manufactured by Electric Field Measurements Corp. (Stockbridge, Mass.). The Gauss meter coil was attached to a Micronta Model 22–182 digital volt meter set on the AC volts scale.

A sample of approximately 500 $\mu$l of the oil/steel particle solution was placed on a piece of 15 point paper board which was suspended in the middle of the coil. The solution had an initial temperature of 12.5° C. measured with an Omega 871 Digital Thermometer. After a period of 30 seconds, the sample was removed and the temperature re-measured. The solution was 87.3° C.

Conclusion: In summary the novel features of this invention include:

The use of electromagnetic fields to induce heating in a seed material and subsequently to induce a thermally triggered gel phase transition.

The use of a magnetically triggered gel to deliver a biologically active material.

The use of a magnetically triggered gel to deliver a reactive chemical or catalyst.

The use of a power electronic inverter to apply a high frequency electromagnetic field to a seeded gel system.

The use of switching power electronics in a gel actuator, sensor, or chemical release or separation system.

The incorporation of a seed material in a gel system.

Note that the electromagnetic fields could be used in a wide variety of ways to trigger a gel phase transition in addition to the technique outlined above. For example, as mentioned previously, microwaves could be used to directly heat the solvent in a gel, with or without the presence of an additional seed material. Also, the use of electromagnetic fields to trigger a phase transition is not limited to the induction of thermal energy in the gel system. For example, it is conceivable that a time-varying electromagnetic field could be used to alter the chemical composition of a seed or solvent, subsequently inducing a phase transition by other than thermal means. Further, the effective electromagnetic fields may also include electromagnetic fields of the oscillating or pulsed type.

It should be appreciated by those skilled in the art that the specific embodiments disclosed above may readily be utilized as a basis for modifying or designing other devices and methods for carrying out the same purpose of the present invention. It should also be realized by those skilled in the art that such equivalent constructions do not depart from the spirit and scope of the invention as set forth in the appended claims.

What is claimed is:

1. A system for remotely inducing a phase transition in a gel, comprising:
    a gel comprising a cross-linked network of polymers swollen in solvent which gel is capable of a phase transition in response to an environmental stimulus;
    a magnetic or electromagnetic receptor in contact with said gel; and
    means for generating a time-varying magnetic field or an electromagnetic field, respectively, in proximity of said gel to produce said environmental stimulus.

2. The system of claim 1, wherein the environmental stimulus comprises a change in temperature.

3. The system of claim 1, wherein the gel phase transition results in release from the gel of a biologically active compound.

4. The system of claim 1, wherein the magnetic receptor has a long dimension and is oriented to optimize the generation of the environmental stimulus.

5. The system of claim 1, wherein said time-varying magnetic field comprises a quasi-static magnetic field.

6. The system of claim 1, wherein said magnetic receptor comprises a ferromagnetic receptor.

7. The system of claim 1, wherein said magnetic receptor comprises an iron-containing derivative.

8. The system of claim 1, wherein said magnetic receptor comprises a material selected from the group consisting of iron, cobalt, nickel, steel, iron oxide, and transition metal ferrites.

9. The system of claim 1, wherein said magnetic receptor is in the form selected from the group consisting of film, rod, particle, fluid, glass-encased particle and bead.

10. The system of claim 1, wherein the gel is a hydrogel.

11. The system of claim 1, wherein the gel is swollen by an is organic solvent.

12. A method of remotely inducing a phase transition in a gel, comprising:
    selecting a gel comprising a cross-linked network of polymers swollen in solvent which gel is capable of a phase transition in response to an environmental stimulus, said gel is placed in contact with a magnetic receptor; and
    applying a time-varying magnetic field in proximity of said gel, said magnetic field generating a response in said magnetic receptor, thereby providing the environmental stimulus which induces said gel to undergo a phase transition.

13. The method of claim 12, wherein the step of applying a time-varying magnetic field comprises applying a quasi-static magnetic field.

14. The method of claim 12, wherein the gel is responsive to a change in temperature.

15. The method of claim 12, wherein application of the time-varying magnetic field induces a phase transition in the gel which results in release from the gel of a biologically active compound.

16. The method of claim 12, wherein the gel selected therein is a hydrogel.

* * * * *